(12) United States Patent
Qin et al.

(10) Patent No.: US 9,294,121 B2
(45) Date of Patent: Mar. 22, 2016

(54) SYSTEM AND METHOD FOR IMPROVING SIGNAL TO NOISE RATIO FOR HIGH FREQUENCY SIGNAL COMPONENT

(75) Inventors: Derek Yong Qin, Andover, MA (US); David Christopher Maurer, Stoneham, MA (US); Clifford Mark Risher-Kelly, Wells, ME (US)

(73) Assignee: Draeger Medical Systems, Inc., Andover, MA (US)

( * ) Notice: Subject to any disclaimer, the term of this patent is extended or adjusted under 35 U.S.C. 154(b) by 0 days.

(21) Appl. No.: 14/370,509

(22) PCT Filed: Jan. 6, 2012

(86) PCT No.: PCT/US2012/020462
§ 371 (c)(1),
(2), (4) Date: Jul. 3, 2014

(87) PCT Pub. No.: WO2013/103353
PCT Pub. Date: Jul. 11, 2013

(65) Prior Publication Data
US 2014/0336948 A1    Nov. 13, 2014

(51) Int. Cl.
| | |
|---|---|
| G01N 33/48 | (2006.01) |
| G01N 33/50 | (2006.01) |
| H03M 3/00 | (2006.01) |
| A61B 5/00 | (2006.01) |
| A61B 5/0428 | (2006.01) |
| H03G 3/00 | (2006.01) |
| G06F 19/00 | (2011.01) |

(52) U.S. Cl.
CPC .............. *H03M 3/49* (2013.01); *A61B 5/0428* (2013.01); *A61B 5/7217* (2013.01); *G06F 19/3406* (2013.01); *H03G 3/001* (2013.01); *H03M 3/44* (2013.01); *H03M 3/486* (2013.01)

(58) Field of Classification Search
CPC .................................................... A61B 5/0428
See application file for complete search history.

(56) References Cited

U.S. PATENT DOCUMENTS

| | | | | |
|---|---|---|---|---|
| 4,356,475 | A * | 10/1982 | Neumann et al. | 340/521 |
| 7,383,080 | B1 * | 6/2008 | Kil et al. | 600/510 |
| 7,942,824 | B1 | 5/2011 | Kayyali et al. | |
| 2002/0099300 | A1 | 7/2002 | Kovtun et al. | |
| 2011/0301428 | A1 | 12/2011 | Fu et al. | |

FOREIGN PATENT DOCUMENTS

EP   0 542 413   5/1993

* cited by examiner

*Primary Examiner* — Russell S Negin
(74) *Attorney, Agent, or Firm* — Jones Day (57) ABSTRACT

An apparatus and method for improving signal to noise ratio of a physiological signal is provided. At least one sensor senses the analog data signal, the analog data signal having a first component including ECG data and a second component including ancillary data. A converter is coupled to the at least one sensor that automatically converts the analog data signal into a digital data signal and decimates the digital data signal from a first sample rate to a second sample rate. A gain compensation circuit is coupled to the converter that automatically measures a magnitude of at least one of the first component and second component of the digital data signal and compares the measured magnitude to a reference value to determine if a gain applied to the analog data signal should be modified and automatically compensates the digital data signal in response to the determination that the analog gain value should be modified, wherein the compensated digital data signal corrects defects associated with a settling period of the converter resulting from modifying the gain applied to the analog data signal.

20 Claims, 8 Drawing Sheets

SYSTEM AND METHOD FOR IMPROVING SIGNAL TO NOISE RATIO FOR HIGH FREQUENCY SIGNAL COMPONENT

The present application is a 35 USC §371 national stage application of International Application No. PCT/US2012/020462, filed Jan. 6, 2012, the entirety of which is incorporated herein by reference.

FIELD OF THE INVENTION

This invention concerns a system and method implemented in patient monitoring devices and, more specifically, for improving signal to noise ratio for high frequency signals detected by an electrocardiogram monitor.

BACKGROUND OF THE INVENTION

In the course of providing healthcare to patients, it is necessary to monitor vital statistics and other patient parameters. An electrocardiogram (ECG) monitor is a device that is selectively coupled to a patient by a plurality of leads that monitor electrical impulses of the patient's heart. The electrical impulses sensed by the leads are used to generate ECG waveform data. ECG waveform data is generally low frequency data. However, in many physiological signals, including ECG signals, data that may be useful in providing patient care can be in more than one frequency band of interest. In the specific case of an ECG monitor, a pacer signal generated by a pacemaker implanted in a patient generates information in the frequency band of 2 KHz to 100 KHz while the ECG signal is from DC to 2 Khz. To obtain both high frequency pacer signal data and low frequency ECG data, the ECG monitor may employ a delta sigma converter to convert both the high frequency as well as the low frequency signal. By running different decimation filters for the two bandwidths, a low resolution, high frequency signal representing the pacer signal can be calculated from the delta sigma data. From the same delta sigma data, a high resolution, low frequency data signal representing an ECG waveform may also be calculated. For example, the high frequency data may have 16 bits of effective resolution at a 64 kilosamples per second (KSPS) rate while the lower bandwidth data may have 24 bits of resolution at a 250 samples per second (SPS) rate.

A performance limitation of a system such as this relates to the noise floor of the high frequency data. Higher sample rates are desirable to measure the narrowest pacemaker pulses. However, there is a tradeoff between the higher sample rate used and the noise floor of the system. As one increases the sample rate, the noise floor of the signal is similarly increased. Moreover, the noise floor is dominated by influence of the delta sigma converter and not the input amplifier. Increasing the gain of the input amplifier will improve the signal to noise ratio accordingly. However, while increasing the gain of the system improves signal to noise ratio, it reduces the dynamic range of the system.

Thus, it is desirable to provide a system that implements an automatic gain control scheme that scales the input amplifier to optimize the acquisition of the high frequency data while leaving the low frequency data undisturbed. A system according to invention principles addresses these and other deficiencies of known systems.

SUMMARY OF THE INVENTION

In a first embodiment, an apparatus and method for improving the signal to noise ratio of an analog data signal is provided. At least one sensor senses the analog data signal, the analog data signal having a first component including patient parameter data and a second component including ancillary data. A converter is coupled to the at least one sensor that automatically converts the analog data signal into a digital data signal and decimates the digital data signal from a first sample rate to a second sample rate. A gain compensation circuit is coupled to the converter that automatically measures a magnitude of at least one of the first component and second component of the digital data signal and compares the measured magnitude to a reference value to determine if a gain applied to the analog data signal should be modified and automatically compensates the digital data signal in response to the determination that the analog gain value should be modified, wherein the compensated digital data signal corrects defects associated with a settling period of the converter resulting from modifying the gain applied to the analog data signal.

In another embodiment, a method of improving the signal to noise ratio of an analog data signal is provided. The method includes converting an analog data signal sensed by at least one sensor to a digital data signal, the analog data signal having a first component including patient parameter data and a second component including ancillary data. The digital data signal is decimated from a first sample rate to a second sample rate and a magnitude of the decimated digital data signal is measured. The magnitude of the decimated digital data signal is compared with a reference value and it is determined if a gain applied to the analog data signal needs to be modified based on the comparison. The decimated digital data signal is automatically compensated in response to determining that the gain applied to the sensed ECG signal is modified and the first and second data components are obtained from the compensated digital data signal.

DETAILED DESCRIPTION

The system and method advantageously improves signal to noise ratio for an input data signal that has two useful components in a first low frequency band and a second high frequency band. In one embodiment, the input data signal is a cardiac data signal that originates from a patient having a pacemaker implanted therein. In this embodiment, the first signal component may include ECG data of a first bandwidth and the second signal component may be pacer data in a second bandwidth that is greater than the first bandwidth. In order to derive patient physiological data from the input signal, the input signal may be received at front end circuitry of device that monitors electrical impulses of a patient. Upon receipt, the input signal may be amplified and converted from an analog signal to a digital signal.

Often times, the input signal includes an amplitude with a broad dynamic range and varying pulse width. To detect signals in the high frequency band, a sampling rate for the signal may need to be increased. However, increasing the sampling rate has a negative effect on a signal output by an analog to digital converter (ADC) such that the noise floor of the signal is also increased. The present system advantageously enables gain to be increased to improve the signal to noise ratio when the input signal is small in magnitude. The system further advantageously minimizes the saturation of the amplifier and/or the ADC when the input signal is large in magnitude. Thus, the system advantageously enables monitoring of the second signal component (e.g. the pacer signal, not the ECG data) on a sample-by-sample basis by dynamically adjusting the gain on the input amplifier (pre-amplifier) to maintain the gain at an optimum level such that the input signal is close to full range, but not saturated. The system further advantageously automatically compensates the signal upon conversion to minimize or remove gain transition artifacts. The result is a system that amplifies the input signal at high sampling rate to obtain the second signal component at the higher frequency while maintaining the quality of the first signal component by automatically compensating for the signal processing (e.g. gain change) required to do so.

Figure 1:
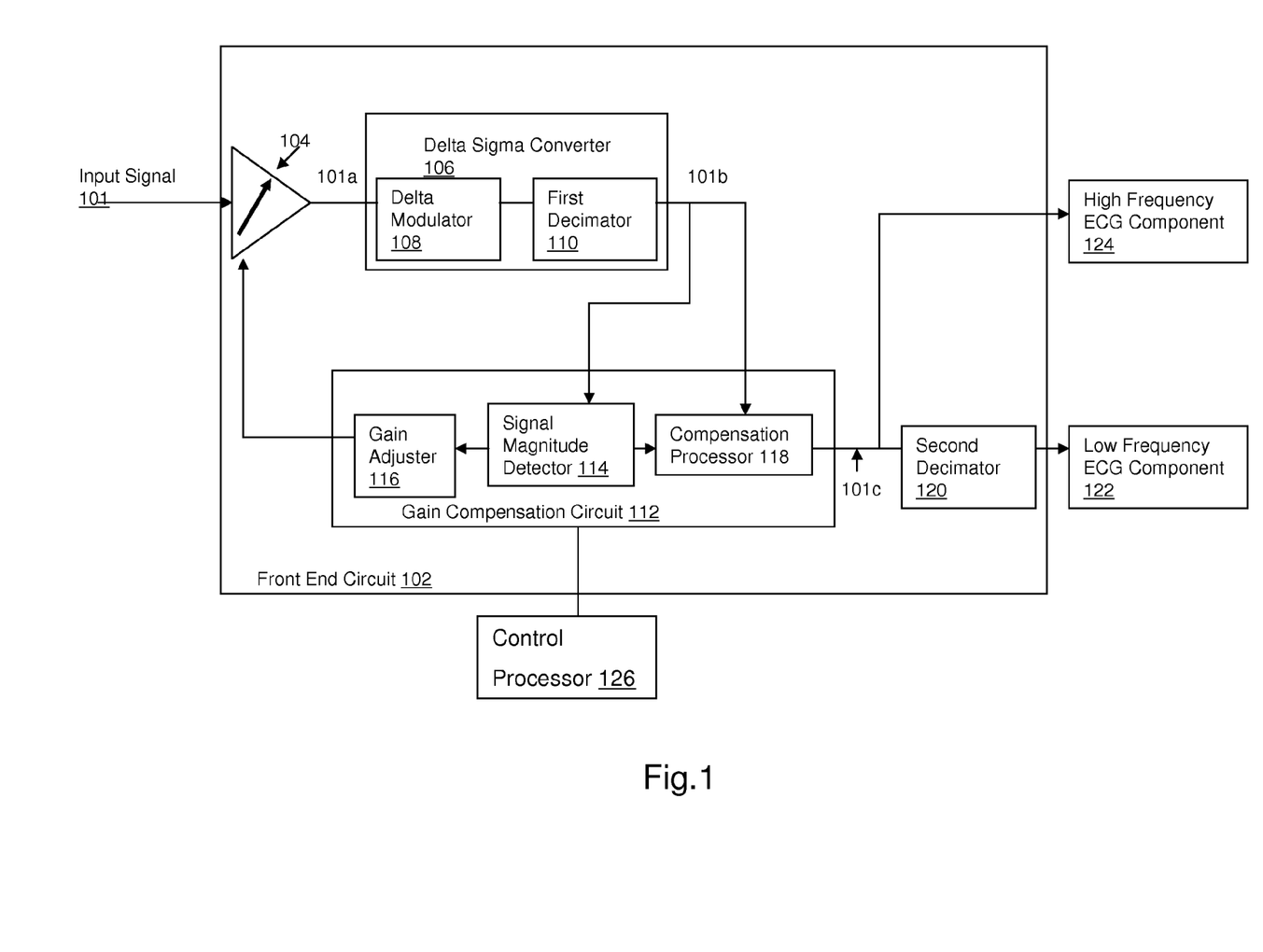
FIG. 1 is an exemplary block diagram of an exemplary ECG front end circuit according to invention principles.

A block diagram of an exemplary front end circuit 102 of a signal monitoring device is shown in FIG. 1. The front end circuit 102 includes circuitry for receiving and processing an input signal 101. The input signal 101 is formed from a plurality of data samples, each data sample including two data components. The first data component is within a first frequency band and the second data component is within a second different frequency band, wherein the second frequency band is greater than the first frequency band. In one embodiment, the front end circuit 102 resides in an ECG monitor and the input signal 101 is a cardiac signal derived from a patient having a pacemaker. In this embodiment, the first data component is a low frequency signal used to generate ECG data and the second data component is a high frequency signal representing pacemaker data. This embodiment is described for purposes of example only and the front end circuit may be employed in any device or system that receives an analog data signal having two different data components in two different frequency ranges. Moreover, this front end circuit 102 be utilized in any patient monitoring device that monitors analog data signals having two components that correspond to different patient physiological parameters. The front end circuit advantageously improves the signal to noise ratio of the signal to derive the patient physiological parameter from the high frequency band without negatively impacting the ability to derive the patient physiological parameter from the low frequency band of the data signal.

The front end circuit 102 may include a variable gain amplifier 104 that may selectively modify the gain applied to the input signal 101 in response to a control signal. The signal modified by the variable gain amplifier 104 is labeled 101a. A delta sigma converter 106 is coupled to an output of the variable gain amplifier 104 and converts the input signal 101a from an analog signal to a digital signal. The delta sigma converter 106 includes a delta modulator 108 that converts the analog input signal 101a into a digital signal. A first decimator 110 is further included in the delta sigma converter 106 and decimates the digital signal from a first frequency (or sample rate) to a second lower frequency (or sample rate) to produce a digital signal 101b. In one embodiment, the input signal 101a enters the delta sigma converter 106 at 2.048 MHz and, after conversion, the first decimator 110 decimates the input signal to be at 32 kilosamples per second (KSPS) to produce the digital signal 101b. This digital signal 101b is needed in order to acquire and monitor the second high frequency data component contained therein.

An output of the first decimator 110 of the delta sigma converter 106 is coupled to a gain compensation circuit 112. The gain compensation circuit 112 includes a signal magnitude detector 114 coupled to each of a gain adjuster 116 and a compensation processor 118. Both the signal magnitude detector 114 and the compensation processor 118 receive the converted digital signal 101b that has been decimated by the first decimator 110. The gain compensation circuit 112 automatically analyzes and processes the decimated digital signal to determine if the gain applied to the input signal 101 or 101b should be modified in order to improve detection of the high frequency second data component of the input signal 101b.

In operation, the gain applied to the input signal 101 and 101b comprises a first gain value (G1) applied to the analog input signal 101 and a second gain value (G2) applied to the digital signal 101b output from the delta sigma converter 106. Except for during a period of transition from one gain value to another, the product of the value of G1 and G2 must equal a fixed total gain, i.e. 1. The gain compensation circuit 112 automatically analyzes a set of data samples from the digital signal 101b in order to determine if the gain applied to subsequent samples from the input signal 101 or 101b should be modified. To determine whether or not the gain applied to input signals 101 or 101b need to be modified, the signal magnitude detector 114 automatically analyzes data samples of input signal 101b to identify the magnitude of each sample. The determined sample magnitude is mapped to a level index, each level index being associated with particular data values for G1 and G2. Upon mapping the determined magnitude to a particular level index, the particular level index is set as a "current level index". The current level index value is compared with a previous level index value of a previous data sample. If the current level index is equal to the previous level index, no gain change is made. If the current level index is not equal to the previous level index, then the values of G1 and G2 are automatically modified by the gain compensation circuit to be equal to values of G1 and G2 associated with the current level index value. The new G1 value is applied by the gain adjuster 116 as a control signal for modifying the gain applied to the analog input signal 101 received at the variable gain amplifier 104. The new G2 value is provided to the compensation processor 118 which applies a gain compensation algorithm to the input signal 101b in order to remove any artifacts that result from the dynamic real-time gain change being applied to the input analog signal 101. The artifacts result from the settling effect of amplifier 104 and the first decimator 110 which requires a predetermined number of samples to be output before the data could be used to proportionally present input signal 101*b*. Thus, when the gain is dynamically changed, a predetermined number of samples reflecting the settling period of the first decimator 110 would be unusable without gain compensation. Gain compensation processor 118 automatically uses G2 as a target gain value to calculate at least one compensated G2 value that are applied to the predetermined samples in the settling period to minimize the distortion and allow both the first low frequency data component and second high frequency data component to be derived from the digital signal even during the settling period.

In response to compensating the digital signal 101*b* by the compensation processor 118 the resulting high frequency second component 124 of input signal 101*c* may be derived and output for further processing or use (e.g. pacer algorithm). Additionally, the compensated signal 101*c* is provided to a second decimator 120 to further decimate the signal and thereby further increasing the resolution of the signal 101*c* to derive the first low frequency data component 122. Thus, the compensated input signal 101*c* advantageously enables derivation of the fixed gain output of the data, even during a settling period associated with the first decimator 110 operation, when the analog gain on the system is dynamically changed.

A control processor 126 is further provided and coupled to the gain compensation circuit 112 enabling selective control of any of the parameters of the gain control and compensation algorithm that is implemented by the system. The control processor 126 may include a predetermined set of control options that may selectively modify an algorithm parameter in response to certain conditions or thresholds being met. Alternatively, the control processor 126 may selectively modify or otherwise control the gain compensation circuit in response to user command. In one embodiment, the control processor 126 may set default gain values for G1 and G2 in response to receiving a user command to do so. This may occur, for example, at device set up prior to any monitoring of the particular patient and may be dependent upon a type of pacemaker implanted in the patient. Additional functions controlled by the control processor 126 will be discussed below with reference to certain aspects of the gain control and compensation algorithm.

In one exemplary embodiment, the front end circuit 102 of the system implements an automatic gain control scheme that selectively scales an input amplifier 104 to optimize the acquisition of the high frequency data in an input signal without disturbing the low frequency data in the input signal. A gain change compensation algorithm is applied by the gain compensation circuit 112. The algorithm is applied to the digital data signal 101*b* output by the delta sigma converter 106 and, in conjunction with a first decimation filter 110, removes any artifacts resulting from dynamically changing gain during system operation. In an exemplary operation, the gain is set as a function of the amplitude of the second signal component (e.g. pacemaker signal). This signal may vary from a few hundred micro-volts to up to ±700 millivolts. When the pacemaker is small (e.g. substantially a few millivolts), the dynamic range of the input signal 101 may be limited to ±320 millivolts. The ±320 millivolts range is derived from the battery effect of electrodes connected to the patient that sense ECG data resulting in an offset from one lead to another. Battery effect results from the gel on the electrodes that are connected to a patient. The gel on the patient electrodes may act as an electrolyte and, when contacting the skin, may generate a high voltage as in a battery (e.g. the voltage may range between 0 and ~0.3 Vdv). When the largest pace pulses are present (e.g. 700 millivolts), these are added to the ±320 millivolts range resulting in a dynamic range requirement substantially equal to ±1 volt. To amplify the analog input signal 101 to improve detection of the high frequency second data component, three gain settings may be used for the gain of the system 4, 8, 12, which corresponds to dynamic ranges of ±1 Volt, ±500 millivolts, ±330 millivolts. The gain applied to the analog input signal 101 by the variable gain amplifier 104 is dynamically changed while the system is running and is set in order to maximize an amplitude of the detected pacemaker signal. When a gain change is initiated, the resulting digital data signal 101*b* is scaled back so that the output of the system always represents a fixed gain for use in any conventional ECG diagnostic and display algorithm. The ECG diagnostic and display algorithm utilizes this data signal to derive, process and display ECG data to a healthcare professional and which is not germane to the present invention. In the case of the high frequency data, this change in gain is initiated between pacemaker events. However, since the digital data signal 101*b* is used to detect pacemaker events, a gain change compensation algorithm applied to the digital data signal 101*b* enables the effects of discontinuities in the data at the time of the gain change to be reduced. Thus, in the case of the low frequency data component, the scaling of data is performed by the compensation processor 118 and occurs before the second decimator 120 further filters the compensated signal 101*c* from 32 KSPS to 250 SPS. The compensation algorithm implemented by the compensation processor 118 advantageously enables the high frequency data to be recovered without any artifact typically associated with dynamically changing the gain of a system. Even though the overall gain of the ECG front end remains fixed at the output, the self-adaptive scheme improves the signal to noise ratio significantly for low amplitude high frequency components, for example, weak pacer signals, while preventing the saturation of the front end circuits.

Figure 2:
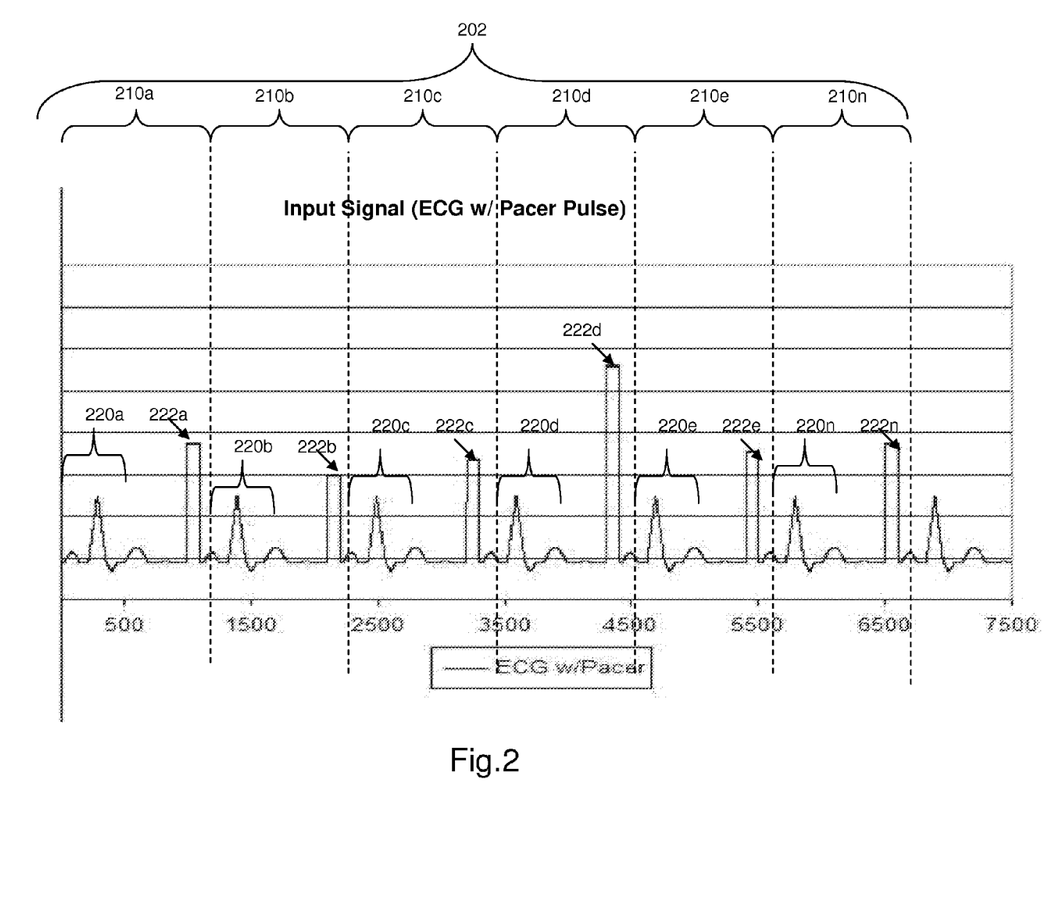
FIG. 2 is an exemplary waveform illustrating data sensed by ECG sensors connected to a patient according to invention principles.

FIG. 2 is a waveform representing the input signal 101*b* that has been converted by the delta sigma converter 106 in FIG. 1. The digital signal 101*b* includes a plurality of successively obtained data samples 210*a*-210*n*. While there are 6 data samples shown herein, this is shown for purposes of example only. The input signal 101*b* may include any number of individual data samples 210. Additionally, FIG. 2 shows the plurality of data samples 210*a*-210*n* may be organized into a set of data samples 202. As shown herein, the set of samples 202 includes 6 individual data samples. However, this too is shown for purposes of example only and the set of data samples 202 may be formed from any number of data samples equal to or greater than 1. Each respective data sample 210*a*-210*n* may include first data components 220*a*-220*n* and second data components 222*a*-222*n*, respectively. Alternatively, a data sample 210*a*-210*n* may only include either the first data component 220*a*-220*n* or the second data component 222*a*-222*n*. In one embodiment, the first data component 220*a*-220*n* may be ECG data in the form of a QRS complex and the second data component 222*a*-222*n* may be pacer signal data derived from a pacemaker in the patient.

Figure 3:
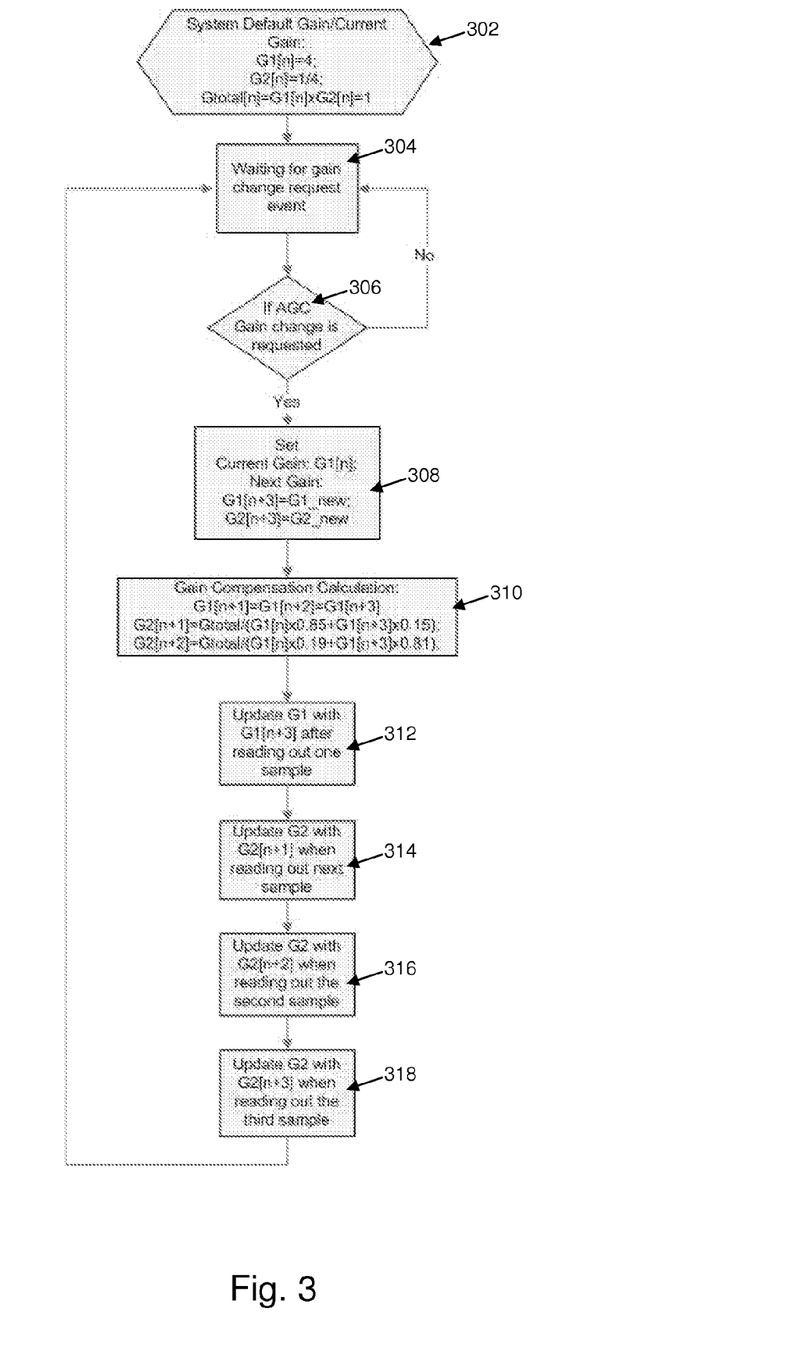
FIG. 3 is a flow diagram detailing an exemplary algorithm for automatically compensating for gain change defects in an input signal according to invention principles.
Figure 4:
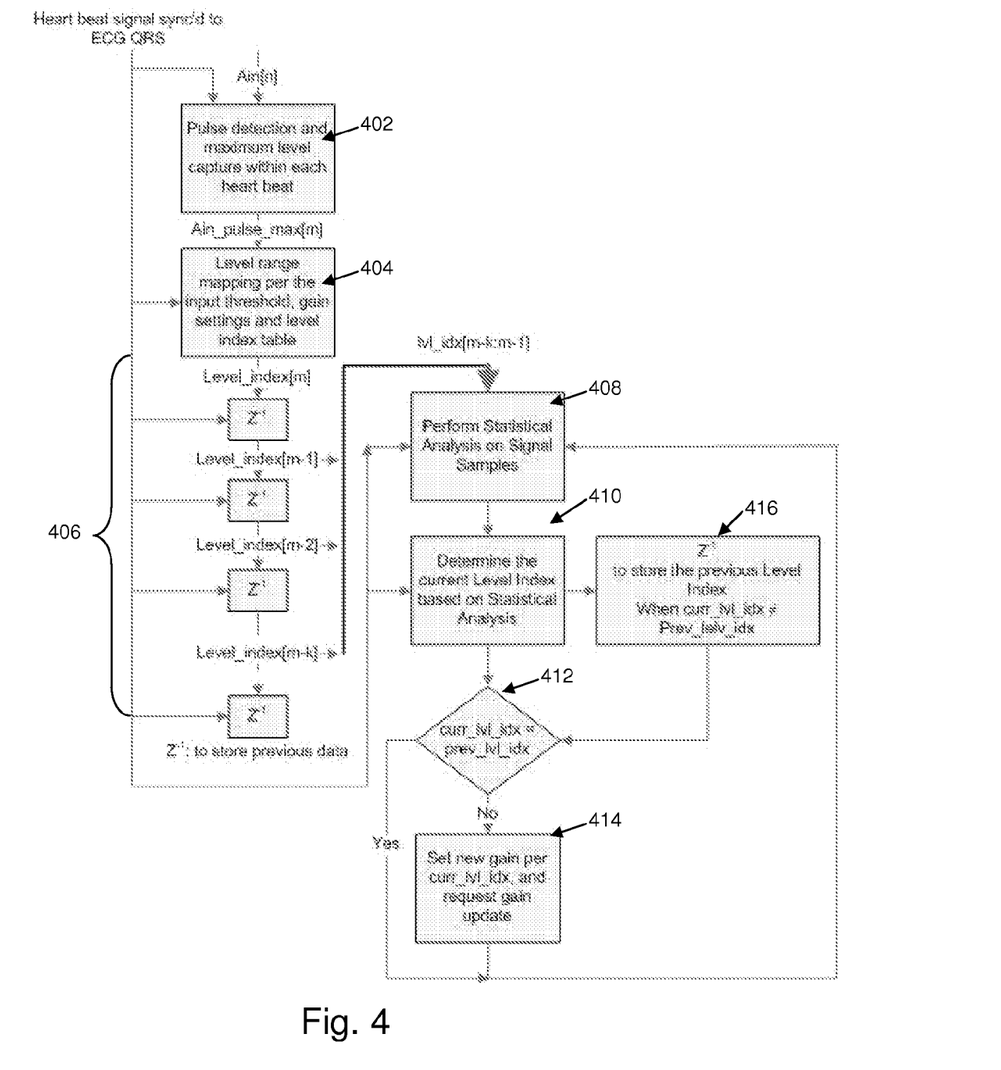
FIG. 4 is a flow diagram detailing an exemplary algorithm for determining if a gain value applied to an input signal should be changed according to invention principles.

An exemplary gain control algorithm applied to the digital signal 101*b* shown in FIG. 2 is detailed in FIGS. 3 and 4. The following description will utilize the elements previously described in FIGS. 1 and 2 for purposes of clarity and understanding.

Referring to FIG. 3, a current gain value is set in step 302. Alternatively, if no samples have been received or patient monitoring has not yet begun, step 302 enables a default gain value to be set for the front end amplifier. The gain value set in step 302 includes setting a first gain value G1 to be applied to at least one sample n of the analog input signal 101 and a second gain value G2 to be applied to the corresponding sample n which is the digital signal 101b produced by the delta sigma converter 106 (FIG. 1). As the system requires a fixed overall gain value, the product of G1 and G2 equals 1, for example, and is represented in FIG. 3 as Gtotal[n]. In the example shown herein, G1[n]=4 and G2[n]=¼. While the fixed overall gain value is described herein as being equal to 1, the total fixed gain may be equal to any positive or negative number depending on the needs and constraints of the system in which the present circuitry is implemented.

As successive data samples n received at the variable gain amplifier 104 are analyzed and converted by the delta sigma converter 106, step 304 waits to receive a gain change request event. The gain change request event is calculated by analyzing at least one data sample from a plurality of data samples output from the delta sigma converter 106 as the digital signal 101b. The algorithm for identifying a gain change event is described with respect to FIG. 4.

FIG. 4 is an exemplary algorithm used to determine if a gain change request event has occurred. The process described herein is synchronized to the QRS complexes 220a-n in respective data samples 210a-n of the digital signal 101b shown in FIG. 2. Thus, the method described in FIG. 4 is applied sequentially to respective data samples in the set of data samples 210a-n. The data samples 210a-n correlate to individual QRS complexes of a patient heartbeat period of a particular patient represented in FIG. 4 as Ain[n]. For each respective sample representing a ECG (Ain[n]) output from the first decimator 110, the signal magnitude detector 114 determines a magnitude of the signal between each respective heartbeats 210a-n. The magnitude of respective heartbeats is determined by identifying a peak having the highest amplitude within the respective heartbeat period. The peak may be either the QRS complex or the pacer signal. Data representing a magnitude value of a respective heartbeat as determined by the signal magnitude detector 114 is represented as Ain_pulse_max[m]. As described herein, index m refers to heat beats and index n refers to individual data samples. This represents the absolute value of the magnitude pulse because the highest peak may be positive or negative.

In step 404, the signal magnitude detector 114 uses a mapping table to map the determined value of Ain_pulse_max[m] to generate a level index for each sample represented as Level_index[m]. An exemplary mapping table is shown below as Table 1.

TABLE 1

Mapping Table

| Ain_pulse_max[m] | G1 | Gtotal | G2 = Gtotal/G1 | Level Index (Level_index) |
|---|---|---|---|---|
| 0.5 | 8 | 1 | 0.125 | 0 |
| 1 | 4 | 1 | 0.25 | 1 |
| 2 | 2 | 1 | 0.5 | 2 |
| 4 | 1 | 1 | 1 | 3 |

The mapping table includes values corresponding to exemplary Ain_pulse_max[m] values, Gain values including total system gain, G1 and G2 and Level Index Values. Each Level_Index value has a particular G1 and G2 value associated therewith and are used in selectively modifying the analog and digital gain value upon determining that the analog gain value is to be modified. The level index column represents the number of different gain configurations that may be applied and is based on the number of gain settings for amplifier 104. Each respective level index includes a value for G1 to be applied to the analog input signal 101 received at the variable gain amplifier and a value for G2 representing the target gain value that is to be applied to the digital signal 101b output from the delta signal converter 106 in order to maintain the value of Gtotal (total system gain) equal to 1. The total system gain being equal to 1 is described for purposes of example only and persons skilled in the art would readily be able to modify the values in Table 1 for implementation in a system that has a total fixed gain other than 1. Additionally, the exemplary embodiment shown herein uses a sigma delta converter 106 having four level indexes and four possible gain configurations that may be applied to the input signal. One skilled in the art would appreciate that a converter having eight, sixteen or thirty two gain levels may be employed and that the mapping table would include a number of level indexes corresponding to a number of available gain values of the pre-amplifier. The number of level indexes does not necessarily improve the outcome of the gain compensation algorithm and so long as the signal is within the acceptable dynamic range of the system, the data converter quantizer compensates for a lower number of level indexes. As the number of index levels increases, the signal to noise ratio is improved accordingly. However, as the number of index levels increases, implementation complexity also increases. Furthermore, increasing the index level may cause more frequent gain update, which may negatively affect system performance. Typically, a system that includes four to eight index levels would sufficiently improve the signal to noise ratio without increasing the complexity or impacting performance of the circuitry.

Figure 5:
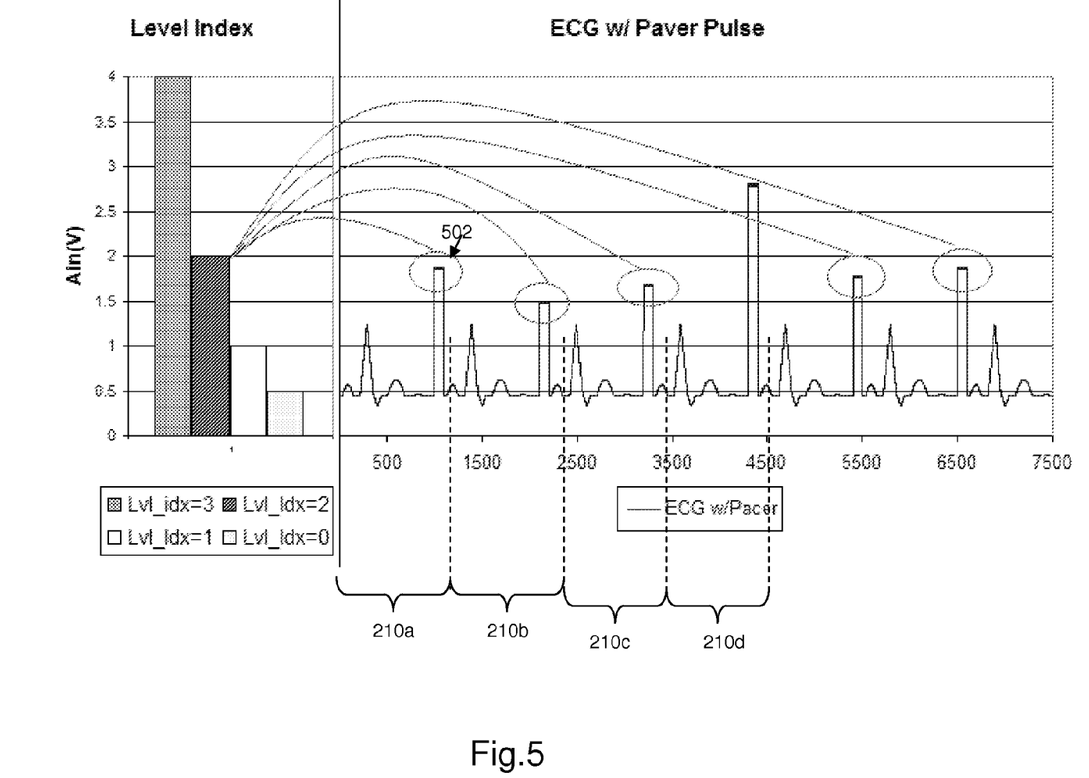
FIG. 5 is a graphical depiction of a plurality of data samples correlated to level indexes used in determining if a gain value applied to an input signal should be changed according to invention principles.

An exemplary operation of the mapping in step 404 in FIG. 4 will now be discussed with respect to FIG. 5. FIG. 5 includes the exemplary waveform shown in FIG. 2 with the addition of a bar graph corresponding to the values of the level_index column in Table 1. As shown herein, Ain[n] is the sample labeled 210a and the value of Ain_pulse_max[m] as determined in step 402 is shown encircled and labeled with reference numeral 502. The value of Ain_pulse_max[m] is substantially 1.80. In step 404, the value of 1.80 representing Ain_pulse_max[m] is compared with the corresponding column in Table 1. As the value determined in step 402 is between 1 and 2, the value is rounded up and the level index value level_index[m] is set equal to 2 as shown by the line connecting circle 502 with the bar on the bar graph that corresponds to level_index=2. As the magnitude analysis of step 402 and level index association of step 404 are performed for every heartbeat period, FIG. 5 also includes the magnitudes for samples 210b-210n which are next heartbeat samples. Thus, when sample 210b become the current sample which corresponds to m and has a magnitude value of Ain_pulse_max[m] and corresponding level index value of level_index[m], the level index for previous sample 210a is stored as level_index[m-1].

Referring back to FIG. 4, upon determining a level index value for the current heartbeat in step 404, a predetermined number of respective level index values associated with a predetermined number of respective heartbeats k that preceded the current heartbeat Ain[n] are gathered and stored in step 406 as a set of data values. As shown herein, the predetermined number of heartbeats k equals 3. Thus, data values corresponding to Ain_pulse_max[m], Ain_pulse_max[m-1]

and Ain_pulse_max[m−2] are stored in storage medium represented as $Z^{-1}$. The value of k is a configurable number that is equal to or greater than 1. This enables a clinician to selectively determine multiple durations of heartbeats between potentially applying a gain change to the system. Additionally, the value of k may be selectively set in response to a control signal generated by the control processor 126 in FIG. 1.

In step 408, a statistical analysis is performed using the set of data values stored in $Z^{-1}$. The statistical analysis may include obtaining at least one of the (a) mean; (b) median; (c) mode; (d) Minimum value; and (e) maximum value corresponding to the level index value for the entire set of data. Upon performing the statistical analysis in step 408, a current level index value is determined in step 410. The current index value is based on the statistical analysis of the set of data as determined in step 410. A determination as to whether the current level index value is equal to a previous level index value is performed in step 412. If the determination in step 412 is negative indicating that the current index value is not equal to the previous index value, then step 414 automatically changes the gain applied to the system. Step 414 includes (a) changing a value of G1 to correspond to the value of G1 in Table 1 associated with the current level index value; and (b) changing the value of G2 to correspond to the values of G2 in Table 1 associated with the current level index value. Upon changing the gain in step 414, the system reverts back to step 408 to repeat the process on a subsequent set of data samples. If the determination in step 412 is positive, then the current level index value determined in step 410 is stored in step 416 and set equal to the previous level index. The current level index value is used in the determination made in step 412 for future sets of data samples and the system reverts back to step 408 to repeat this process on subsequent sets of data samples.

In an exemplary operation, and referring back to FIG. 5, the set of data values stored for use in determining a current level index value (step 406) may include the level index values for samples 210a, 210b and 210c. The statistical analysis may include determining a mode of level index values for samples 210a-210c. The index value corresponding to the mode of samples 210a-210c is 2 and the current level index value is set equal to 2. The current level index value is then compared to a previous level index value and, if the values are not equal, a new gain value is set and a gain change is requested. For example, if the current level index value is 2 and the previous level index value is 1, this would initiate a gain change and the gain values of G1 and G2 would be modified and set equal to the values of G1 and G2 that correspond with the column labeled "level_index" having a data value of 2 as shown in table 1. In this example, the gain value for G1 would be changed from 4 to 2 and the gain value for G2 would change from 0.25 to 0.5.

In response to requesting a dynamic gain change, the values of G1 and G2 for the upcoming heartbeats (e.g. n+1, n+2 and n+3, where n is the heartbeat sample for which the gain change request has been received) will be modified. Thus, the gain value G2 for each of samples n+1, n+2 and n+3 of the digital signal 101b output by the sigma delta converter 106 are automatically modified by the gain compensation circuit 112. Compensating the digital signal 101b is necessary to continue to obtain usable data due to the inherent settling period associated with the first decimator 110 of the delta sigma converter 106. Typically, in response to a gain change request, G1 and G2 are modified automatically and the immediate change to the gain value G2 would result in glitch in the output data contained in digital data signal 101b. To remedy this, the gain compensation circuit 112 automatically modifies the G2 value being applied at the output of the delta sigma converter over a predetermined number of samples (e.g. the number of samples being equal to the settling period) to be less than the original value of G2[n] but greater than the target G2 value G2_new. This step-down compensation alleviates discontinuities in the data that may be caused by the settling period that is normally associated with the first decimator 110 and which occurs following the dynamic gain change. This stepped compensation algorithm will now be described referring back to the flow diagram of FIG. 3. The following exemplary algorithm details an embodiment whereby the gain level is stepped down until it reaches the target gain value. However, one skilled in the art would recognize that there may be instances where the target G2 value may be higher than the current G2 value and the compensation algorithm may need to step up the values of G2 until the targeted G2 is reached Referring again back to FIG. 3, the system is currently awaiting a gain change request event in step 304 as determined by the algorithm described above in FIG. 4. A determination is made in step 306 as to whether or not dynamic gain change has been requested for sample n. If the determination is negative, the algorithm reverts back to step 304. If the determination in step 306 is positive and a gain change event has been requested, step 308 automatically determines a number of samples [s] equal to the settling period of the first decimator 110 and automatically assigns new gain values G1_new and G2_new to be equal to sample n+s. In the embodiment described in FIG. 3, the number of samples in the settling period s is equal to 3. Therefore, if a gain change request occurs on sample n, step 306 sets the current gain value G1[n] and adds a number of samples equal to the number of samples in the settling period s to n to identify to which subsequent sample the new gain values will apply. As the settling period is 3 samples, the new gain value G1_new is set equal to G1[n+3] and the new gain value G2_new is set equal to G2[n+3].

A gain compensation calculation is performed in step 310. The gain compensation calculation may be performed using a linear equation as shown in FIG. 3. Alternatively, the calculation may be performed using a non-linear equation. Because the total gain value that includes the first gain value (G1) and the second gain value (G2) must remain fixed, a dynamic change to the value of G1 between successive samples also requires a corresponding change to the value of G2 at the same time. However, the first decimator 110 of the delta sigma converter is unable to immediately decimate the converted input signal 101b when an immediate change to G1 has been implemented. The gain compensation calculation in step 310 enables the samples decimated during the settling period to remain viable and enables the system to extract both low frequency ECG data and high frequency pacer data from the samples during the settling period. The gain compensation calculation sets a value for G1[n+s] equal to G1_new. The gain compensation algorithm automatically modifies the value for G2 for the sample periods n+1 and n+2 so as to remove any gain change artifacts. For respective samples occurring during settling period s, the gain value G2 is determined by dividing the total gain of the system Gtotal by the sum of the product of the current gain G1[n] and a first compensation constant C1 and the product of target gain G1[n+s] and a second compensation constant C2.

For example, where s is equal to 3, the value of G2 for the first sample in the settling period G2[n+1] is equal to the total gain of the system Gtotal divided by the product of the current gain G1[n] and the first compensation constant C1 and the product of the target gain G1[n+3] and the second compensation constant C2, wherein the sum of the first compensation constant C1 and second compensation constant C2 is equal to 1 and wherein value of the first compensation constant C1 is greater than the value of the second compensation constant C2.

The value of G2 for the second sample in the settling period G2[n+2] is equal to the total gain of the system Gtotal divided by the product of the current gain G1[n] and the first compensation constant C1 and the product of the target gain G1[n+3] and the second compensation constant C2, wherein the sum of the first compensation constant C1 and second compensation constant C2 is equal to 1 and wherein value of the first compensation constant C1 is less than the value of the second compensation constant C2. This advantageously enables the gain compensation circuit to apply a gain value to the digital signal that is between the current gain value and target gain during the settling period associated with the delta sigma converter.

In one embodiment, the first compensation constant C1 applied to sample G2[n+1] ranges between 0.75 and 0.95 and the second compensation constant C2 applied to sample G2[n+1] ranges between 0.05 and 0.25. In this embodiment, the first compensation constant applied to sample G2[n+2] ranges between 0.10 and 0.30 and the second compensation constant applied to sample G2[n+2] ranges between 0.70 and 0.90.

In another embodiment, the first compensation constant C1 applied to sample G2[n+1] is 0.85 and the second compensation constant C2 applied to sample G2[n+1] is 0.15. In this embodiment, the first compensation constant applied to sample G2[n+2] is 0.19 and the second compensation constant applied to sample G2[n+2] is 0.81.

Once the G2 values for the first and second samples in the settling period [n+1] and [n+2] are determined in step 310, the system automatically updates the first gain value G1 applied at the variable gain amplifier 104 to be equal to G1_new (e.g. G1[n+3]) after reading out the first sample [n] in step 312. The second gain value G2 is updated when reading out the first sample [n+1] in step 314 to be equal to the value of G2[n+1] as determined in the calculation performed in step 310. In step 316, the system further updates the second gain value G2 after reading out a second sample [n+2] to be equal to the value of G2[n+2] as determined in the calculation performed in step 310. The value of G2 is further automatically updated in step 318 to be equal to G2[n+3], which reflects the target second gain value G2_new associated with the target first gain value G1_new. After updating the G2 value in step 318, the system reverts back to step 304 to wait for a gain change request event.

Figure 6:
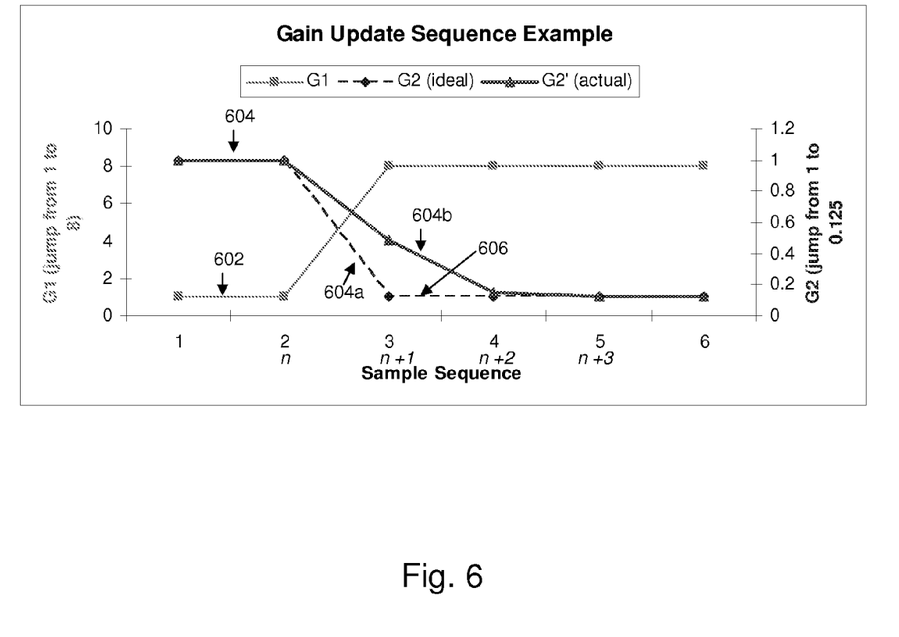
FIG. 6 is a graphical depiction illustrating an exemplary change in analog and digital gain values over a predetermined period of data samples according to invention principles.

An example of the gain compensation calculation performed in steps 310-318 in FIG. 3 is graphically represented in FIG. 6. The graph of FIG. 6 includes a horizontal axis representing successive samples of ECG data over a predetermined period of six (6) samples. A scale on the first vertical axis represents the analog gain values of G1 and a scale on the second vertical axis parallel to the first vertical axis represents the values of the digital gain G2 applied to the signal output from the first decimator 110. The plot shown in FIG. 6 is a graphical representation of the result of a gain change request event occurring between Sample 2 and Sample 3 requesting that the value of the analog gain G1 be changed from 1 to 8 and the resulting value of digital gain G2 being modified from 1 to 0.125 in order to maintain the system at a fixed constant gain equal to 1. The analog gain value G1 over samples 1-6 is represented by the plot labeled 602. At Samples 1 and 2, the analog gain value G1 is equal to 1. Thus, Sample 2 represents the value of G1[n] described in FIG. 3. Upon reaching Sample 3 (G1[n+1] in FIG. 3), the gain change request has been implemented thereby changing the value of the analog gain G1 from 1 to the target analog gain value of 8 (e.g. G1_new). Continuing the association with FIG. 3, Samples 4 and 5 in FIG. 6 correspond to G1[n+2] and G1[n+3], respectively and are similarly set equal to 8.

The digital gain value G2 during Sample periods 1 and 2 is represented by the line labeled 604. The digital gain value G2 during Sample 2 is equal to G2[n] in FIG. 3. Thus, the values of Samples 3-5 correspond to the values G2[n+1], G2[n+2] and G2[n+3], respectively. Upon implementation of the gain change request between Samples 2 and 3, two distinct plots emerge from the line labeled 604 in Sample 2 and illustrates the advantageous operation of the gain compensation algorithm. The ideal value of the digital gain G2 (e.g. G2_new in FIG. 3) is 0.125 and is represented by the line labeled 604a. The ideal digital gain value G2 is 0.125 in order to maintain the total gain of the system (Gtotal) constant and equal to 1. However, the first decimator 110 of the delta sigma converter 106 would generate noisy unusable data if the ideal digital gain value G2 represented by line 606 was implemented immediately during Sample 3 (e.g. during sample n+1). The gain compensation algorithm of step 310 is performed and produces a plot representing the actual compensated digital gain values G2 implemented during successive Samples 3-6 (e.g. n+1 . . . n+3) in response to the analog gain value G1 being set equal to 8. The plot showing the actual compensated digital gain values G2 is represented by the line labeled 604b. During Sample 3, the actual compensated digital gain value G2 is set equal to G2[n+1] as calculated in step 310 in FIG. 3. The value of G2[n+1] is substantially at a midpoint between the original digital gain value G2[n] and the target digital gain value G2_new. During Sample 4, the value of G2 is set equal to G2[n+2] as calculated in step 310 of FIG. 3 resulting in a digital gain value G2 that is substantially closer to the ideal target digital gain value G2_new. The settling period for the first decimator 110 ends at Sample 5 and the digital gain value G2 value in Sample 5 is set equal to the target digital gain value of G2_new (0.125). This step down process advantageously removes any artifacts associated with the gain change performed and allows certain types of data to be determined from the data samples occurring during the settling period.

Figure 7:
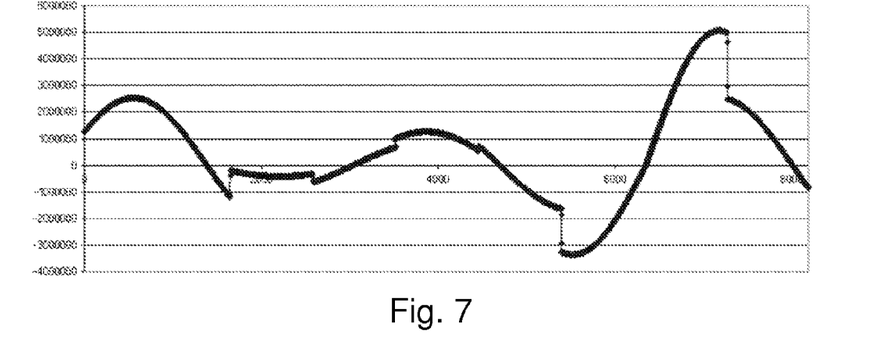
FIG. 7 is an exemplary waveform illustrating the input signal without compensating a digital gain value of an input signal.
Figure 8A:
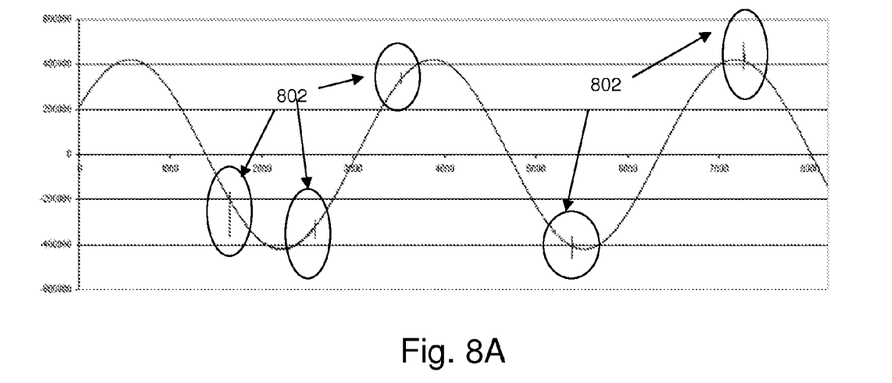
FIG. 8A is an exemplary waveform illustrating the input signal having its digital gain value compensated according to invention principles.
Figure 8B:
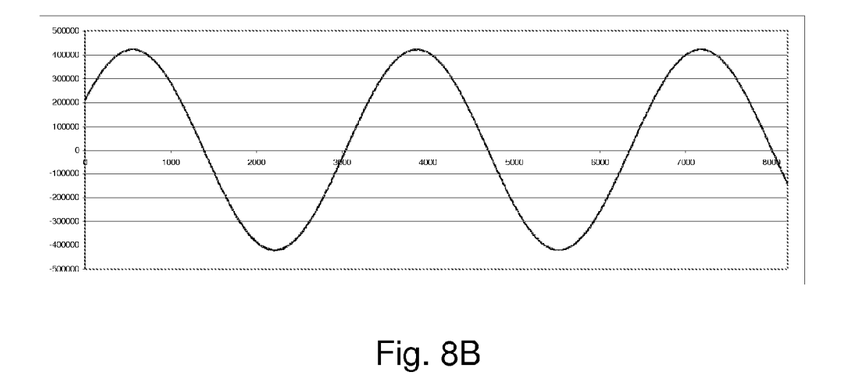
FIG. 8B is an exemplary waveform illustrating the input signal having its digital gain value compensated for the transition period artifacts according to invention principles.

FIG. 7 represents an exemplary plot of low frequency data derived from data samples that occur within the settling period of the first decimator without the gain change compensation algorithm being implemented. As can be seen in FIG. 7, the waveform shown herein is jagged and discontinuous at certain portions thus preventing this data from being usable to derive low frequency ECG information from the patient without knowing at which point of time G1 is modified. Contrast the curve shown in FIG. 8 which represents an exemplary waveform simply derived from data samples by gain correction to make the total gain equal to a fixed gain value. The result are a plurality of glitches shown in the circles labeled 802 in FIG. 8A. These are caused by the gain change artifacts. FIG. 8b which represents an exemplary wave form derived from data samples during the same settling period but having been compensated by the gain change compensation algorithm described above. The result is a waveform unencumbered by noise or disruption caused by gain change artifacts. The resulting compensated data samples are then able to be used for pacer detection algorithm, and further decimated by the second decimator 120 to derive low frequency ECG data for the patient.

Figure 9A:
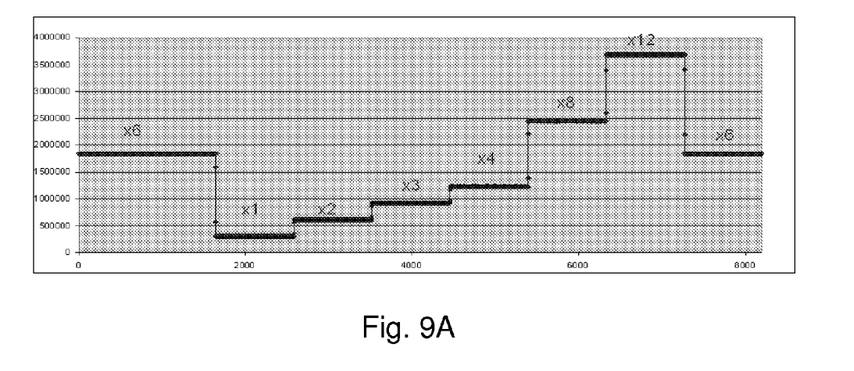
FIGS. 9A-9B are graphical depictions of an input signal and associated noise having undergone a plurality of gain change events according to invention principles.
Figure 9B:
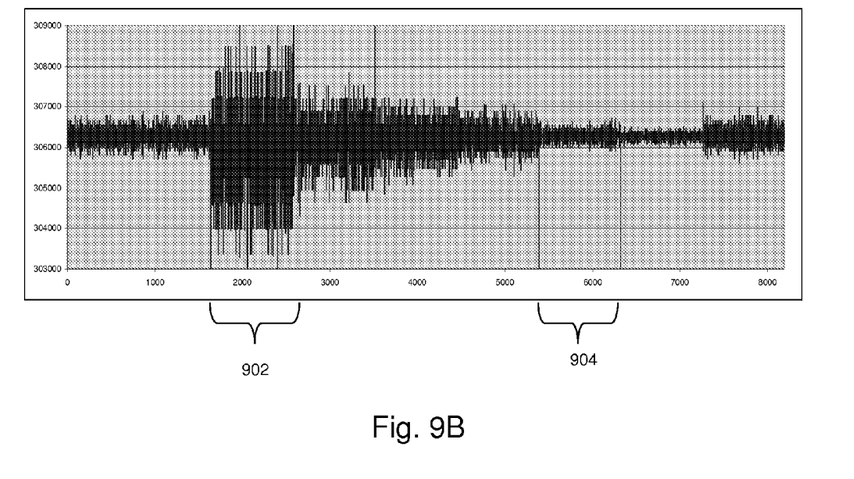

Additional advantages provided by the algorithm implemented by the gain compensation circuit 112 in FIG. 1 can be seen when looking at FIGS. 9A and 9B which are graphical representations of the effect on the digital input signal 101b (in FIG. 1) when the analog gain of the system is changed. The plots in FIGS. 9A and 9B are aligned in time (in milliseconds) along the horizontal axis in order to visually see the effect of changing the analog gain of the system. FIG. 9A is a plot showing the effect on the digital data signal 101b when different analog gain values are applied to the input signal of the system. The analog gain value is modified to be equal to values 6, 1, 2, 3, 4, 8, 12 and back to 6. Between each change in analog gain value, there are two sample periods representing the settling period of the system during which no data is available. The advantages of increasing the analog gain value on the input signal for the system can be seen in the graph of FIG. 9B.

FIG. 9B illustrates the noise associated with the input signal 101b after gain compensation has been performed. Greater signal noise is illustrated by highly variable peaks having greater amplitudes and thus a higher magnitude. An exemplary signal having a large noise component is shown in the section labeled 902 and corresponds to an analog gain value of 1. It is desirable to reduce the noise of the signal and minimize the magnitude of the signal in order to identify weaker signals representing high frequency, low amplitude pace pulses in the heartbeat signal of a patient with a pacemaker. An example of a desirable signal with a reduced noise level from which high frequency, low amplitude data can be derived is shown in the section labeled 904. This section of the input signal 904 corresponds to an analog gain value of 8. Thus, when looking at FIGS. 9A and 9B it is readily apparent that a lower gain results in higher noise and vice versa which is why it is advantageous to dynamically modify the gain on an input signal. Further, because of the negative effect on signal quality resulting from dynamically changing the gain, it is also advantageous to implement the presently described gain compensation algorithm to ensure that there are no discontinuities in the data during the transition period between gain changes.

The apparatus and algorithms described above with respect to FIGS. 1-9 advantageously enable the analog gain applied to an input signal to be dynamically modified in order to improve the signal to noise ratio of the input signal and still obtain high frequency, low amplitude data from the signal after conversion from an analog signal to a digital signal. This advantage holds true even during a settling period associated with a decimator of an analog to digital converter due to the automatic gain change compensation performed on samples of the digital signal that occur during the settling period to gradually step down a digital gain value applied to the digital signal until the target digital gain value has been reached. The apparatus automatically evaluates a set of prior input signals to determine if the analog gain value for subsequent data samples needs to be changed by detecting a magnitude of each sample of an input signal determining a level index associated with the determined magnitude. The apparatus performs a statistical analysis using the level indexes associated with a set of previous data samples and compares the current level index to the previous level index to determine if they are equal. If they are not equal, the analog gain of the system is advantageously changed in order to improve the signal to noise ratio in the case of weak input signal in the system. In response to changing the analog gain of the system, the gain compensation algorithm is implemented on data samples during the settling period associated with the decimator thereby enabling high frequency, low amplitude data (e.g. pace pulse data) to be derived therefrom as well as enable the data samples to be further decimated to determine low frequency data (e.g. ECG data).

Although the invention has been described in terms of exemplary embodiments, it is not limited thereto. Rather, the appended claims should be construed broadly to include other variants and embodiments of the invention which may be made by those skilled in the art without departing from the scope and range of equivalents of the invention. This disclosure is intended to cover any adaptations or variations of the embodiments discussed herein.

What is claimed is:

1. An apparatus for improving signal to noise ratio of an analog data signal derived from at least one physiological sensor coupled to a patient, the apparatus comprising:
   at least one sensor that senses the analog data signal, the analog data signal having a first component including patient parameter data and a second component including ancillary data;
   a converter coupled to the at least one sensor that automatically converts the analog data signal into a digital data signal and decimates the digital data signal from a first sample rate to a second lower sample rate, the converter comprising circuitry; and
   a gain compensation circuit coupled to the converter including circuitry that automatically measures a magnitude of at least one of the first component and second component of the digital data signal, the gain compensation circuit including circuitry that compares the measured magnitude to a reference value to determine if a gain applied to the analog data signal should be modified and automatically compensates the digital data signal in response to the determination that the analog gain value should be modified, wherein the compensated digital data signal corrects defects associated with a settling period of the converter resulting from modifying the gain applied to the analog data signal such that the first component and the second component can be derived from the digital signal even during the settling period, the first component and the second component characterizing a physiological condition of the patient.

2. The apparatus as recited in claim 1, wherein said converter is a delta sigma converter including a first decimator that decimates the digital data signal from the first sample rate to the second sample rate.

3. The apparatus of claim 2, wherein said first sample rate is substantially 2 MSPS and said second frequency is substantially 32 KSPS.

4. The apparatus of claim 1, wherein the patient parameter data of the first data component includes an ECG waveform having a low frequency associated therewith and the ancillary data of the second data component includes pace pulse data derived from a pacemaker.

5. The apparatus of claim 1, further comprising a filter coupled to the converter for further decimating the digital data signal from the second sample rate to a third frequency sample rate, wherein the third sample rate is lower than the first and second sample rate.

6. The apparatus of claim 5, wherein the digital data signal at the second sample rate is used to identify the ancillary data and the digital data signal at the third sample rate is used to identify ECG waveform data associated with the patient.

7. The apparatus of claim 1, wherein the digital data signal includes a plurality of individual data samples representing respective heartbeats of the patient; and the gain compensation circuit automatically measures a magnitude for respective ones of the plurality of data samples and compares the measured magnitude to the reference value to determine if the gain value applied to the analog data signal should be modified.

8. The apparatus of claim 7, wherein the gain compensation circuit determines if the analog gain value should be changed by analyzing a predetermined number of data samples to identify a magnitude of the respective data samples and mapping the measured magnitudes to a level index having respective analog and digital gain values associated therewith and determining if the mapped level index is equal to a level index of a previous set of data samples and; storing the mapped level index if the mapped level index is equal to the level index of the previous set of data samples; and generating a gain change request signal if the mapped level index is not equal to the level index of the previous set of data samples.

9. The apparatus as recited in claim 8, wherein said gain compensation circuit automatically modifies at least one of (a) a gain value applied to the analog data signal using the analog gain value associated with the mapped level index; and (b) a gain value applied to the digital data signal using the digital gain value associated with the mapped level index in response to the gain change request signal.

10. The apparatus of claim 1, wherein the reference value is derived by performing a statistical analysis of previously received digital data signals, wherein the statistical analysis includes performing at least one of (a) a mode analysis; (b) a mean analysis; (c) a median analysis; (d) a maximum analysis; and (e) a minimum analysis.

11. The apparatus as recited in claim 1, wherein the gain compensation circuit generates the compensated digital data signal by identifying a number of data samples in the settling period of the converter and modifying a digital gain value of respective samples in the settling period to be between a current gain value and a target gain value, the target gain value being a number that, when multiplied by the modified analog gain value equals a fixed total gain value.

12. The apparatus as recited in claim 1, wherein the gain compensation circuit generates the compensated digital data signal by determining a gain value to be applied to the digital data signal (G2) by dividing a value representing a total gain of the system (Gtotal) by a sum of the product of a current gain value applied to the analog data signal G1 [n] and a first compensation constant C1 and the product of target gain applied to the analog data signal G1 [n+s] and a second compensation constant C2, where n is the current sample and s is a number of samples in the settling period.

13. A method of improving the signal to noise ratio of an analog data signal derived from at least one physiological sensor coupled to a patient, the method comprising:
converting an analog data signal sensed by at least one sensor to a digital data signal, the analog data signal having a first component including patient parameter data and a second component including ancillary data;
decimating the digital data signal from a first frequency to a second frequency, measuring a magnitude of the decimated digital data signal;
comparing the magnitude of the decimated digital data signal with a reference value; determining if a gain applied to the analog data signal needs to be modified based on the comparison; and
automatically compensating the decimated digital data signal in response to determining that the gain applied to the sensed digital data signal is modified; and
obtaining the first and second data components from the compensated digital data signal, wherein the compensated digital data signal corrects defects associated with a settling period of the converter resulting from modifying the gain applied to the analog data signal, such that the first component and the second component can be derived from the digital signal even during the settling period, the first component and the second component characterizing a physiological condition of the patient,
wherein at least one of the converting, the decimating, the comparing, and the compensating is performed by circuitry.

14. The method of claim 13, wherein said decimated digital data signal includes a plurality of data samples, and said activity measuring the magnitude of the decimated digital data signal further comprises measuring a magnitude of at least one of the first component and second component of respective data samples to identify a maximum magnitude level associated with respective ones of the plurality of data samples.

15. The method of claim 14, wherein said activity of compensating further comprises automatically identifying an analog gain value and digital gain value associated with the mapped level index; and automatically modifying the analog gain applied to the analog data signal and the digital gain applied to the digital data signal using the mapped analog and digital gain values.

16. The method of claim 14, wherein said activity of compensating further comprises identifying a number of data samples in the settling period of the analog to digital converter; and modifying a digital gain value of respective samples in the settling period to be between a current gain value and a target gain value, the target gain value being a number that, when multiplied by the modified analog gain value equals a constant gain value.

17. The method of claim 13, wherein said decimated digital data signal includes a plurality of data samples representing respective heartbeats of a patient, each respective data sample includes heartbeat data, and said activity measuring the magnitude of the decimated digital data signal further comprises measuring a magnitude of at least one of the first component and second component of the heartbeat data to identify a maximum magnitude level associated with respective ones of the plurality of data samples.

18. The method of claim 13, wherein said activity of comparing further comprises mapping a maximum magnitude level for each data sample to an level index, each level index having an analog gain value and digital gain value associated therewith; and comparing mapped level indexes for a set of data samples with a reference value; determining if the mapped level index is equal to the reference value; and initiating a gain change request if the mapped level index is not equal to the reference value.

19. The method of claim 18, wherein the reference value includes a mapped level index associated with at least one prior received data sample.

20. The method of claim 18, further comprising the activity of identifying a number of data samples to be included in a set of data samples; and performing a statistical analysis on the set of data samples using respective mapped level indexes of respective data samples in the set; and determining a mapped level index for the set of data sample for use in comparing to the reference value.

* * * * *